US 6,623,587 B1
United States Patent
Muller et al.

Date of Patent: Sep. 23, 2003

(54) METHOD FOR MAKING FIBROUS LOOP MEMBER

(75) Inventors: Jorg Muller, Karben (DE); Gabriele Stiehl, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/762,088

(22) PCT Filed: Aug. 13, 1999

(86) PCT No.: PCT/US99/18440

§ 371 (c)(1), (2), (4) Date: Feb. 28, 2001

(87) PCT Pub. No.: WO00/09057

PCT Pub. Date: Feb. 24, 2000

(30) Foreign Application Priority Data

Aug. 13, 1998 (EP) .............................................. 98115225

(51) Int. Cl.[7] .................................................. B31F 1/22
(52) U.S. Cl. ....................... 156/207; 156/178; 156/210; 264/287; 604/380
(58) Field of Search ............................... 156/178, 199, 156/205, 207, 209, 176, 201, 462, 210; 428/182, 183; 264/287; 604/379, 380, 391

(56) References Cited

U.S. PATENT DOCUMENTS

| 5,256,231 A | * | 10/1993 | Gorman et al. | 156/178 |
| 5,656,232 A | * | 8/1997 | Takai et al. | 264/518 |
| 5,681,302 A | * | 10/1997 | Melbye et al. | 604/373 |
| 5,888,607 A | * | 3/1999 | Seth et al. | 428/92 |

FOREIGN PATENT DOCUMENTS

| EP | 0 626 159 A1 | 4/1994 |
| EP | 0 738 505 A1 | 10/1996 |
| WO | WO 95/05139 | 2/1995 |

OTHER PUBLICATIONS

PCT WO 94/27813 Dec. 1995 Morley, Timothy.*

* cited by examiner

Primary Examiner—Michael W. Ball
Assistant Examiner—John L. Goff
(74) Attorney, Agent, or Firm—Michael P. Hayden; Ken K. Patel

(57) ABSTRACT

The present invention relates to a method of making a fibrous loop member which can be used in disposable absorbent articles such as diapers, adult incontinence devices, sanitary napkins, and the like. The fibrous loop member includes a backing and a sheet of fibers which has arcuate portions projecting from the backing.

11 Claims, 3 Drawing Sheets

METHOD FOR MAKING FIBROUS LOOP MEMBER

FIELD OF THE INVENTION

The present invention relates to a method for making fibrous loop members which are useful in disposable absorbent article such as diapers, adult incontinence products, sanitary napkins and the like. The fibrous loop member of the present invention comprises a backing and a sheet of fibers having arcuate portions.

BACKGROUND OF THE INVENTION

Disposable absorbent articles such as diapers and adult incontinence product are well known in the art. Such disposable absorbent articles collect and retain urine and fecal material deposited thereon by the wearer.

To date, most attempts in the art to handle the urine and fecal material collected and retained in the disposable absorbent article have been directed to handling urine. Dealing with fecal material collected by the disposable absorbent article is simply more difficult than dealing with urine, due to the complex rheology of low-viscosity material.

Prior art attempts to deal with fecal material include providing a first topsheet which conforms closely to the wearer and has an aperture. The aperture is hopefully registered with the anal opening, so that fecal material passes therethrough into a void space. The first topsheet may comprise various elastic panels in order to closely conform to the skin of the wearer, and/or may have linear elastic strands. Improvements have been made in this area of the prior art, such as optimizing the material properties of the first topsheet. Such optimization makes the first topsheet more comfortable to the wearer and allows a single disposable absorbent article to fit a larger range of sizes of wearers.

Yet other attempts have been made in this area of the prior art to provide an absorbent core with a hole therein, in order to receive the fecal material. The hole may be oblate shaped, so that it is longer and narrower than the aperture in the first topsheet, or may be diamond shaped. The hole in the core may be positioned below an aperture which has elastic strips around its edge.

Improvements to this genre of the prior art disposable absorbent articles also include the addition of spacers. Spacers may be interposed between the first topsheet and the core, in order to ensure a void space is present to receive the fecal material.

Yet other attempts have been made in this genre of the prior art to provide barriers which limit the movement of fecal material to particular portions of the disposable absorbent article. The barriers limit the contact of the fecal material to a lesser portion of the skin of the wearer, than a comparable disposable absorbent article which has no barriers.

Still other attempts in the prior art provide barrier leg cuffs which are upstanding from the plane of the topsheet. The barrier leg cuffs prevent fecal material from breaching the perimeter of the disposable absorbent article.

Examples of such attempts to handle fecal material include U.S. Pat. No. 4,892,536 issued Jan. 9, 1990 to DesMarais et al.; U.S. Pat. No. 4,909,803 issued Mar. 20, 1990 to Aziz et al.; U.S. Pat. No. 4,968,312 issued Nov. 6, 1990 to Khan; commonly assigned U.S. Pat. No. 4,990,147 issued Feb. 5, 1991 to Freeland; commonly assigned U.S. Pat. No. 5,037,416 issued Aug. 6, 1991 to Allen et al.; U.S. Pat. No. 5,062,840 issued Nov. 5, 1991 to Holt et al.; commonly assigned U.S. Pat. No. 5,171,236 issued Dec. 15, 1992 to Dreier et al.; and European Patent Application 0,355,740 A2 published Feb. 28, 1990 to Enloe.

However, none of these attempts to handle fecal material solve the problem of low-viscosity fecal material which is prevalent in younger children, particularly those who are breast fed. Low-viscosity fecal material easily migrates within the disposable absorbent article under the influences of gravity and motion or pressure by the wearer.

The migration of the fecal material often moves it towards the perimeter of the disposable absorbent article, increasing the likelihood of leakage. The migration of the fecal material also smears it against the skin of the wearer, making cleanup more difficult. In order to clean the wearer, the caretaker must wipe the entire area of the skin which has encountered the fecal material and typically has to deal with a relatively large soiled area.

One attempt in the art to handle low-viscosity fecal material is found in European Patent Application EP-A-714272 filed in the name of Roe. This application is a disposable absorbent article having a high trans topsheet capacity.

Another attempt to handle low viscosity fecal material is found PCT Patent Application PCT/US97/20840 filed in the name of Bast et al.. This application is a disposable absorbent article having a fibrous loop member and a method of making such a fibrous loop member.

It is an object of the present invention to provide an enhanced method for making a fibrous loop member that is particularly suitable in disposable absorbent article.

SUMMARY OF THE INVENTION

It is an object of the present invention to provide a method for making a fibrous loop member which may be used as a fecal management member in a disposable absorbent article. The method comprises the steps of providing a sheet of fibers, forming said sheet of fibers so that it has anchor portions defining a surface and arcuate portions unidirectionally projecting from that surface, bonding the anchor portions to a backing, and deforming the arcuate portions.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

DETAILED DESCRIPTION OF THE INVENTION

Figure 1:
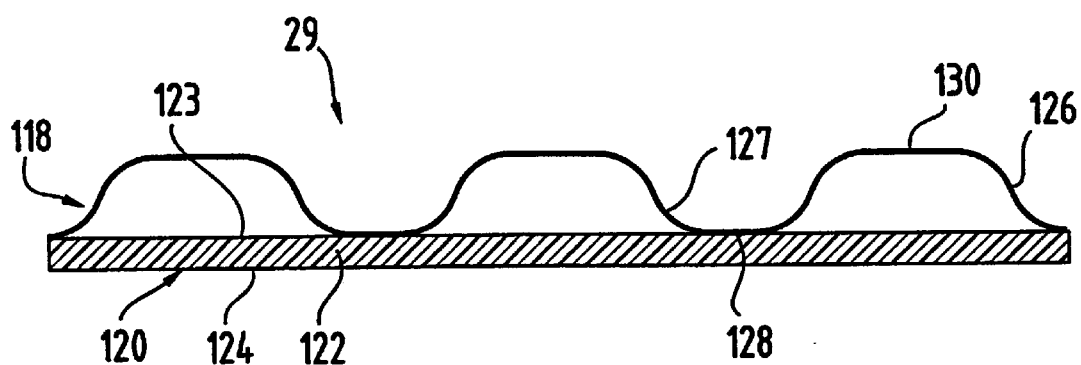
FIG. 1 is a schematic side view of a fibrous loop member of the present invention.

FIG. 1 illustrates an embodiment of a fibrous loop member made according to the method of the present invention, generally designated by the reference numeral 29.

The deformation of the arcuate portions may improve the wearing comfort of articles comprising the fibrous loop member according to the present invention by enhancing the force and pressure distribution when the fibrous loop member is in direct or indirect contact with the body of the wearer.

The fibrous loop member made according to the method of the present invention is particularly useful as a fluid management member and/or fecal management member in disposable absorbent articles such as diapers, adult incontinence devices (e.g. garments, pads, bed pads), sanitary napkins, and the like. As used herein, the term "fluid management member" refers to devices which are intended to handle fluids in particular aqueous fluids such as body exudates (e.g. urine, menses, sweat, pus, and the like). As used herein, the term "fecal management member" refers to a fluid management member particularly suitable for highly viscous body exudates such as feces and menses. The term "handling fluids" as used herein refers to capabilities such as to acquire fluids, to distribute fluids, to store liquids, to retain fluids, or the like. As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A typical disposable absorbent article comprises a liquid pervious topsheet, a liquid impervious backsheet joined to the topsheet, and an absorbent member positioned intermediate the topsheet and the backsheet. The fibrous loop member preferably is joined to the backsheet with the backing side facing towards the backsheet. The topsheet may cover at least a part of the fibrous loop member such that this part of the fibrous loop member is positioned intermediate the topsheet and the backsheet. The topsheet may also cover the whole of the fibrous loop member. Alternatively, a disposable absorbent article may comprise only a backsheet, a fibrous loop member joined to said backsheet, and preferably an absorbent member intermediate the backsheet and the fibrous loop member in which case the fibrous loop member may serve as a topsheet.

The fibrous loop member made according to the method of the present invention may also be used as the loop member in a mechanical fastening system of the hook and loop type.

Generally, the fibrous loop member 29 is a sheet of loop material 118 having a backing 120 preferably comprising a thermoplastic backing layer 122 (e.g., of polypropylene) having front and rear major surfaces 123 and 124, and a multiplicity of longitudinally oriented fibers in a specially formed sheet of fibers 126 having generally non-deformed anchor portions 127 bonded by being embedded in the backing layer 122 at spaced elongate generally parallel bonding locations 128 that are continuous in one direction along the front surface 123 with arcuate portions 130 of the sheet of fibers 126 projecting from the front surface 123 of the backing layer 122 between the bonding locations 128 in continuous rows also extending transversely across the sheet of loop material 118. The arcuate portions 130 of the sheet of fibers 126 have a generally uniform height from the backing layer 122 of greater than about 0.5 millimeters and preferably greater than about 1.0 millimeters, the height of the formed sheet of fibers 126 is at least one third, and preferably one half to one and one half times the distance between the bonding locations 128, the individual fibers in the sheet of fibers 126 are less than 25 denier (preferably in the range of 1 to 10 denier) in size, and the sheet of fibers 126 without the backing 120 has a basis weight in the range of 5 to 300 grams per square meter (and preferably in the range of 15 to 100 grams per square meter) measured along the first surface 123 to provide sufficient open area between the fibers in the sheet of fibers 126 along the arcuate portions 130 (i.e., between about 10 and 90 percent open area) to afford ready penetration of fecal material into the individual fibers along the arcuate portions 130.

Suitable materials for use as the backing 120 include but are not limited to thermoplastic films, porous films, apertured films, apertured formed films, unapertured formed films, nonwoven webs, breathable materials, such as breathable films, including but not limited to microporous films, apertured nonwoven webs, scrims and the like.

The term "scrim" as used herein refers to a network of fibers or strands comprising at least two substantially parallel fibers or strands running in a first direction and at least two substantially parallel fibers or strands running in a second direction. At least some of the fibers or strands running in the first direction are connected to at least some of the fibers or strands running in the second direction at the respective cross-over points. The angle between first and second direction is at least 30°, preferably 45°, more preferably 60°, most preferably 90°. A scrim may comprise fibers or strands of different shapes, compositions and dimensions.

Preferably, the backing is made of thermoplastic polymers. The backing 120 is preferably a relatively thin layer having a thickness in the range of about 0.00125 to 0.025 centimeters.

The fibers in the sheet of fibers 126 can be disposed in various directions with respect to the parallel bonding locations 128 and may or may not be bonded together at crossover points in the arcuate portions 130; can be disposed in various directions with respect to the parallel bonding locations 128 with the majority of the fibers in the sheet of fibers 126 (i.e., over 80 or 90 percent) extending in directions at about a right angle to the bonding locations 128; or all of the individual fibers in the sheet of fibers 126 can extend in directions generally at right angles to the spaced generally parallel bonding locations 128.

Sheet of fibers 126 preferably has a hydrophilicity which is less than the hydrophilicity of the backing 120. In a preferred embodiment, the sheet of fibers themselves have a hydrophilicity gradient wherein the arcuate portions 130 have a hydrophilicity which is less than the hydrophilicity of the bonded locations 128. Even in this configuration it is preferred that the bonded locations 128 of the sheet of fibers 126 have a hydrophilicity which is less than the hydrophilicity of the backing 120.

The arcuate portions 130 of the sheet of fibers 126 may comprise additional fibers. The additional fibers are joined to the sheet of fibers 126 either by thermo-bonding or by adhesive bonding. Suitable techniques to attach the additional fibers to the sheet of fibers are meltblowing the additional fibers onto the sheet of fibers 126 or flocking the additional fibers onto the sheet of fibers 126. The additional fibers may be flocked to the whole of the sheet of fibers 126 or only to a portion of the sheet of fibers 126, the portion comprising at least some of the arcuate portions 130. Preferably the length of the additional fibers is less than the height of the arcuate portions 130 over the backing. The basis weight of the additional fibers may be homogenous or it may vary in different portions of the sheet of fibers. Preferably, the basis weight of the additional fibers is between 1 gram per square meter and 100 gram per square meter. Many different types of additional fibers are suitable for use in the present invention. Suitable fibers include natural fibers (modified or unmodified), as well as synthetically made fibers. Examples of suitable unmodified/modified natural fibers include cotton, Esparto grass, bagasse, hemp, flax, silk, wool, wood pulp, chemically modified wood pulp, jute, rayon, ethyl cellulose, and cellulose acetate. Suitable synthetic fibers can be made from polyolefins such as polyethylene (e.g. PULPEX™) or polypropylene, polyamides such as nylon, polyester such as DACRON™ or KODEL™, polyethyleneterepthalate, polyvinyl chloride, polyvinyl fluoride, polytetrafluoroethylene, polyvinylidene chloride, polyacrylics such as ORLON™, polyvinyl acetate, polyethylvinyl acetate, non-soluble or soluble polyvinyl alcohol, polyurethanes, polystyrenes, and the like. The additional fibers may comprise solely natural fibers, solely synthetic fibers, or any compatible combination of natural and synthetic fibers. Preferably, the additional fibers are selected from the group of: polyester, polyamide, polyethylene, polypropylene, polyethyleneterepthalate. These fibers have been used widely in fibrous loop members because of their favorable combination of raw material properties such as resiliency and durability, their ease of conversion, and their cost, and the like.

The arcuate portions of the fibrous loop member of the present invention may comprise a surface coating agent. As used herein, the term "surface coating agent" refers to any substance or composition that is covering at least part of the surface of the arcuate portions of the sheet of fibers.

Preferably, the surface coating agent of the present invention is an silicone-containing composition and/or an oil-containing composition. Other suitable surface coating agents include, but are not limited to, fluorinated materials such as fluoropolymers (e.g., polytetrafluoroethylene (PTFE), commercially available under the trade name TEFLON™), and chlorofluoropolymers. Other materials which may prove suitable as a surface coating agent for the present invention include latexes, paraffins, and the like.

A silicone containing composition suitable for the present invention is a silicone release coating available from Dow Coming of Midland. Mich. USA, under the designation Syl-Off 7677 to which a cross-linker available as Syl-Off 7048 is added preferably in proportions of 100 parts to 10 parts, respectively. Another suitable silicone containing composition is a UV curable silicone comprising a blend of two silicones commercially available from General Electric Company, Silicone Products Division, of Waterford, N.Y., USA, under the designations UV 9300 and UV 9380C-D1, preferably in proportions by weight of 100 parts to 2.5 parts, respectively.

Examples of suitable oil containing compositions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotioned Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysilozane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The oil-containing composition may also be deployed in such a way that it is only released at the time of intended use such as being microencapsulated.

To be the most effective in the handling of low-viscosity fecal material the fibrous loop member must have a lofted open structure. One key component of this equation is the height of the arcuate portions 130 of the sheet of fibers 126 from the backing 120. As mentioned above the arcuate portions 130 of the sheet of fibers 126 have a generally uniform height from the backing 120 of greater than about 0.5 millimeters and preferably greater than about 1.0 millimeters. While even greater heights would provide excellent handling of low-viscosity fecal material, e.g., heights of 5.0 centimeters, such heights would create unwanted bulk in the diaper which may cause discomfort for the wearer.

The other key component is the resiliency of the fibrous loop member 29, more particularly the resiliency of the sheet of fibers 126. In order to remain open, the sheet of fibers 126 must have a sufficient resiliency to withstand the forces of packaging and those applied by the wearer. Preferably, the sheet of fibers 126 has a resiliency of at least 50% after 30 seconds under an applied force of 100 g/cm2, more preferably, the sheet of fibers 126 has a resiliency of at least 75% after 30 seconds under an applied force of 100 g/cm2, most preferably, the sheet of fibers 126 has a resiliency of at least 85% after 30 seconds under an applied force of 100 g/cm2.

The anchor portions 127 are preferably of such dimension that a planar circle having a diameter of from about 0.2 millimeters to about 20 millimeters may be inscribed thereon, more preferably, the anchor portions 127 are preferably of such dimension that a planar circle having a diameter of from about 0.2 millimeters to about 10 millimeters may be inscribed thereon, and most preferably, the anchor portions 127 are preferably of such dimension that a planar circle having a diameter of from about 0.2 millimeters to about 5 millimeters may be inscribed thereon.

By including the step of deforming the arcuate portions according to the method of the present invention, a larger variety of shapes is available in the manufacture of fibrous loop members according to the present invention.

Preferably, the step of deforming said arcuate portions comprises temporary compression of the arcuate portions. Due to the thermoplastic nature of the fibers in the sheet of fibers, a temporary compression may lead to permanent or at least long lasting deformation of the arcuate portions.

Preferably, the arcuate portions of the sheet of fibers have a temperature of more than 40° Celsius, more preferably than 50° Celsius, even more preferably more than 60° Celsius, most preferably more than 80° Celsius. The temperature of the fibers may have remained from the making of the fibers (e.g. extrusion) or may be achieved by externally heating the fibers (e.g. by hot air).

Figure 2:
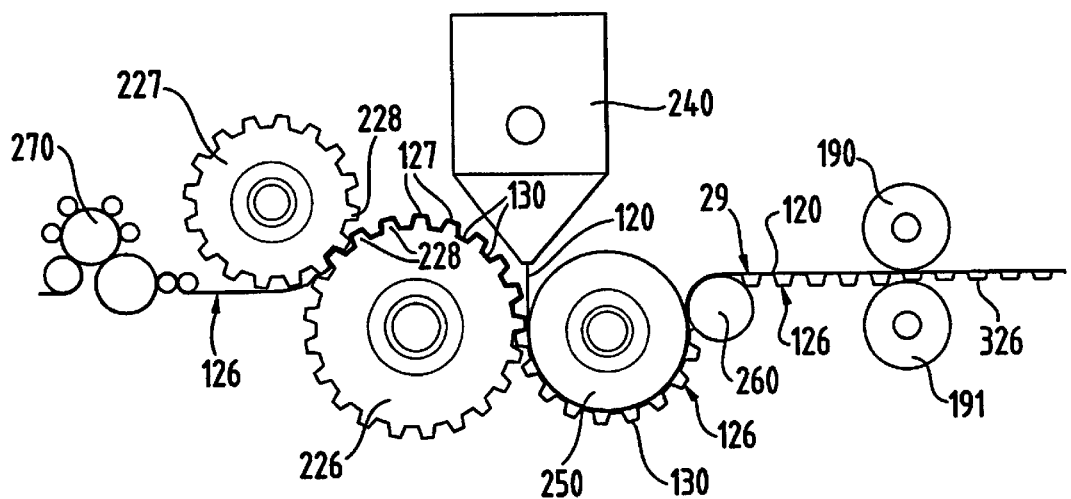
FIG. 2 is a schematic illustration of a method and equipment for making the fibrous loop member of the present invention.

FIG. 2 schematically illustrates a method and equipment for forming the fibrous loop member 29. The method illustrated in FIG. 2 generally comprises the steps of providing a sheet of fibers, forming the sheet of fibers 126 so that it has anchor portions 127 defining a surface 123 and arcuate portions 130 unidirectionally projecting from that surface, bonding the anchor portions 127 of the sheet of fibers 126 projecting from the surface 123 to backing 120, and deforming the arcuate portions 130 of the sheet of fibers 126.

This method is performed by providing first and second heated corrugating members or rollers 226 and 227 each having an axis and including a plurality of circumferentially spaced generally axially extending ridges 228 around and defining its periphery, with the ridges 228 having outer surfaces and defining spaces between the ridges 228 adapted to receive portions of the ridges 228 of the other corrugating member 226 or 227 in meshing relationship with the sheet of fibers 126 between the meshed ridges 228 and to afford rolling engagement between the ridges 228 and spaces of the corrugating members in the manner of gear teeth. The corrugating members 226 and 227 are mounted in axially parallel relationship with portions of the ridges 228 of the corrugating members 226 and 227 meshing generally in the manner of gear teeth; at least one of the corrugating members 226 or 227 is rotated; and the sheet of fibers 126 is fed between the meshed portions of the ridges 228 of the corrugating members 226 and 227 to generally conform the sheet of fibers 126 to the periphery of the first corrugating member 226 and form the arcuate portions 130 of the sheet of fibers 126 in the spaces between the ridges 228 of the first corrugating member 226 and the generally parallel anchor portions 127 of the sheet of fibers 126 along the outer surfaces of the ridges 228 on the first corrugating member 226. The formed sheet of fibers 126 is retained along the periphery of the first corrugating member 226 after it has moved past the meshed portions of the ridges 228. The thermoplastic backing layer 120 is formed and bonded to the anchor portions 127 of the sheet of fibers 126 on the end surfaces of the ridges 228 on the first corrugating member 226 by extruding the thermoplastic backing layer 120 (e.g., polypropylene) in a molten state from a die 240 into a nip between the anchor portions 127 of the sheet of fibers 126 on the periphery of the first corrugating member 226 and a cooling roll 250 after which the fibrous loop member 29 is separated from the first corrugating member 226 and carried partially around the cooling roll 250 and through a nip between the cooling roller and a pinch roller 260 to complete cooling and solidification of the thermoplastic backing layer 120. The arcuate portions 130 are deformed by feeding the fibrous loop member between a first compressing roll 190 and a second compressing roll 191 having an axis substantially parallel to the axis of the first compressing roll. After passing the compressing rolls, the arcuate portions 326 of the sheet of fibers are deformed.

The sheet of fibers 126 fed between the meshed portions of the ridges 228 of the corrugating members 226 and 227 can be in the form of yarns distributed so that the fibers in the sheet of fibers 126 fed between the meshed ridges 228 of the corrugating members 226 and 227 are uniformly distributed across the width of the sheet of fibers 126 and all extend generally perpendicular to the axes of the corrugating members 226 and 227, or the fibers in the sheet of fibers 126 can be disposed in random orientation as in a non woven web or sheet. Such a nonwoven sheet of randomly oriented fibers 126 with no internal bonding except for the friction between the fibers can be formed from loose fibers using a carding machine 270 as illustrated, which nonwoven sheet of randomly oriented fibers 126 has enough integrity to be fed from the carding machine 270 into the nip between the corrugating members 226 and 227 (if needed, a conveyer (not shown) could be provided to help support and guide the non woven sheet of randomly oriented fibers 126 is used, preferably the first corrugating member 226 has a rough finish (e.g., formed by sand blasting), the second corrugating member 227 has a smooth polished finish, and the first corrugating member 226 is heated to a temperature slightly above the temperature of the second corrugating member 226 SO that the nonwoven sheet of fibers 126 will preferentially stay along the surface of the first corrugating member 226 and be carried to the nip between the first corrugating member and the cooling roller 250 after passing through the nip between the corrugating members 226 and 227.

Corrugating members 226 and 227 adapted to have such a sheet of fibers 126 fed into them can have their ridges 228 oriented generally in the range of 0 to 90 degrees with respect to their axes, but preferably have their ridges 228 oriented at 0 degrees with respect to (or parallel to) their axes which simplifies making of the corrugating members 226 and 227.

Preferably, the first compressing roll 190 and the second compressing roll 191 are mounted such that there is a distance between the two facing surfaces of the rolls. More preferably, the distance is at least 10% of the initial height of the arcuate portions 130 of the sheet of fibers 126, even more preferably more than 20% of the initial height of arcuate portions, even more preferably 30% of the initial height of arcuate portions, most preferably more than 50% of the initial height of arcuate portions. As used herein, the term "initial height" of the arcuate portions refers to the height of the arcuate portions from the backing during the bonding of the anchor portions of the sheet of fibers to the backing.

Instead of extruding a solid thermoplastic sheet 120 from die 240, a plurality of fibers may be extruded from a die to form a backing layer.

Instead of extruding a thermoplastic material from a die such as die 240, a non-molten backing may be used. The roller 250 is then heated to thermo-bond the backing to the sheet of fibers.

Preferably, the drives for the corrugating member 226 and 227 and for the cooling roller 250 are separately controllable so that the cooling roller 250 can be rotated at a surface speed that is the same as or different than the surface speed of the first corrugating member 226. When the cooling roller 250 and the first corrugating member 226 are rotated so that they have the same surface speed, the sheet of fibers 126 will have about the same shape along the backing 120 as it had along the periphery of the first corrugating member 226 as is illustrated in FIGS. 2 through 5. When the cooling roller 250 and the first corrugating member 226 are rotated so that the cooling roller has a surface speed that is slower than the surface speed of the first corrugating member 226 the anchor portions 127 of the sheet of fibers 126 will be moved closer together in the backing layer 120 at the nip between the cooling roller 250 and the first corrugating member 226, resulting in greater density of the loop portions 130 along the backing 120 than when the cooling roller 250 and the first corrugating member 226 are rotated so that they have the same surface speed. This technique of increasing the amount of loop portions 130 or the loop population is useful both to make fibrous loop members having different numbers of loop portions 130 per centimeter of backing length using the same equipment, and to make fibrous loop members with more loop portions 130 per centimeter of backing length than could be formed between ridges 228 machined on the corrugating member 226 and 227 because of physical limitations in machining such ridges 228 close together.

Figure 3:
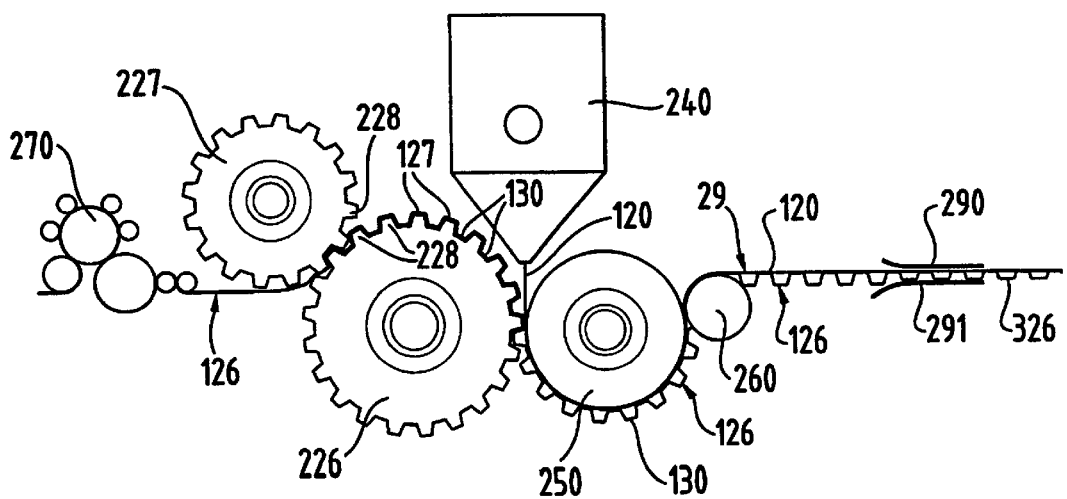
FIG. 3 is a schematic illustration of a second embodiment of a method and equipment for making the fibrous loop member of the present invention.

FIG. 3 shows a second embodiment of the method and equipment of the present invention for forming a fibrous loop member, which method is generally similar and uses much of the same equipment as is illustrated in FIG. 2., except that the step of deforming the arcuate portions is carried out by feeding the fibrous loop member through a first plate 290 and a second plate 291 substantially parallel to said first plate. The plates are mounted such that there is a distance between the facing inner surfaces of the first plate 290 and of the second plate 291. Preferably, the distance between the inner surfaces of the first plate and the second plate is at least 10% of the initial height of arcuate portions, more preferably more than 20% of the initial height of arcuate portions, even more preferably 30% of the initial height of arcuate portions, most preferably more than 50% of the initial height of arcuate portions. After passing the plates, the arcuate portions 326 of the sheet of fibers are deformed.

Figure 4:
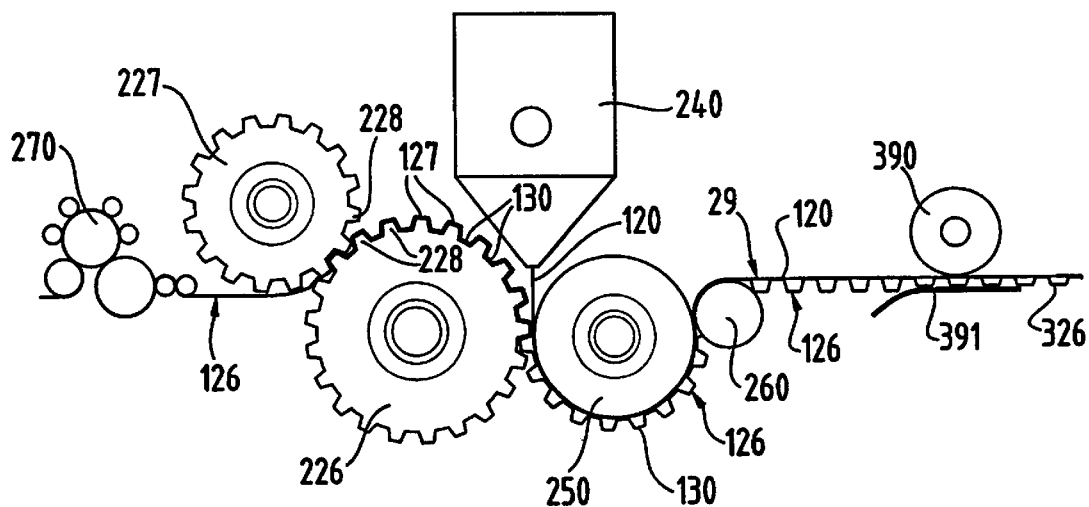
FIG. 4 is a schematic illustration of a third embodiment of a method and equipment for making the fibrous loop member of the present invention.

FIG. 4 shows a third embodiment of the method and equipment of the present invention for forming a fibrous loop member, which method is generally similar and uses much of the same equipment as is illustrated in FIG. 2., except that the step of deforming the arcuate portions is carried out by feeding the fibrous loop member between a compressing roll 390 and plate 391. The compressing roll 390 and the plate 391 are mounted such that there is a distance between the facing surfaces of the compressing roll and the plate. Preferably, the distance between the facing surfaces of the compressing roll 390 and the plate 391 is at least 10% of the initial height of arcuate portions, more preferably more than 20% of the initial height of arcuate portions, even more preferably 30% of the initial height of arcuate portions, most preferably more than 50% of the initial height of arcuate portions. After passing the compressing roll and the plate, the arcuate portions 326 of the sheet of fibers are deformed.

Figure 5:
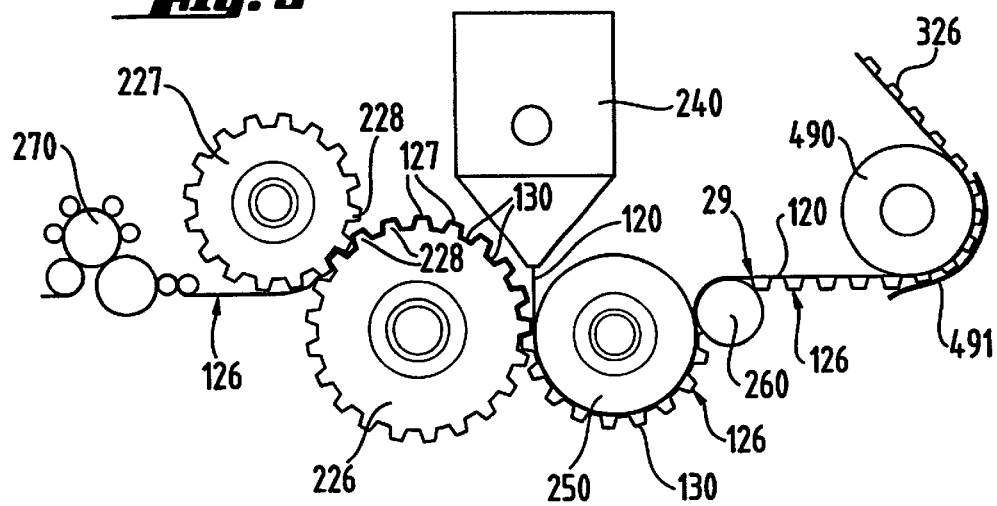
FIG. 5 is a schematic illustration of a fourth embodiment of a method and equipment for making the fibrous loop member of the present invention.

FIG. 5 shows a fourth embodiment of the method and equipment of the present invention for forming a fibrous loop member, which method is generally similar and uses much of the same equipment as is illustrated in FIG. 2., except that the step of deforming the arcuate portions is carried out by feeding the fibrous loop member between a compressing roll 490 and curved plate 491 which is concentric with the compressing roll. The compressing roll 490 and the curved plate 491 are mounted such that there is a distance between the facing surfaces of the compressing roll and the curved plate. Preferably, the distance between the facing surfaces of the compressing roll 490 and the curved plate 491 is at least 10% of the initial height of arcuate portions, more preferably more than 20% of the initial height of arcuate portions, even more preferably 30% of the initial height of arcuate portions, most preferably more than 50% of the initial height of arcuate portions. After passing the compressing roll 490 and the curved plate 491, the arcuate portions 326 of the sheet of fibers are deformed.

What is claimed is:

1. A method for making a fibrous loop member comprising the steps of providing a sheet of thermoplastic fibers, forming said sheet of fibers so that it has anchor portions defining a surface and arcuate portions unidirectionally projecting from said surface, bonding said anchor portions to a backing, and thereafter thermoplastically deforming said arcuate portions, wherein the arcuate portions are at a temperature of greater than 40° C. at the beginning of the step of deforming.

2. A method for making a fibrous loop member according to claim 1 wherein said sheet of fibers comprises longitudinally oriented fibers.

3. A method for making a fibrous loop member according to claim 1 wherein said step of deforming said arcuate portions comprises temporary compression of said arcuate portions.

4. A method for making a fibrous loop member according to claim 3 wherein said temporary compression during said deformation step is carried out by a first compressing roll and a second compressing roll opposite said first compressing roll, said sheet of fibers and said backing being fed between said first compressing roll and said second compressing roll.

5. A method for making a fibrous loop member according to claim 4, said arcuate portions having an initial height defined as the height of the arcuate portions from the backing during said step of bonding wherein the space between the surface of said first compressing roll and the surface of said second compressing roll is at least 10% of said initial height of said arcuate portions.

6. A method for making a fibrous loop member according to claim 3 wherein said temporary compression during said step of deforming is carried out by a first plate and a second plate parallel to said first plate, said fibrous loop member being fed between said first plate and said second plate.

7. A method for making a fibrous loop member according to claim 6, said first plate and said second plate each having an inner major surface, said inner surfaces being in facing relation each other, said arcuate portions having an initial height defined as the height of the arcuate portion from the backing during said step of bonding wherein said inner surface of said first plate has a distance from said inner surface of said second plate of at least 10% of the initial height of said arcuate portions.

8. A method of making a fibrous loop member according to claim 3 wherein said temporary compression during said deforming step is applied by a roll and a plate, said fibrous loop member being fed between said roll and said plate.

9. A method of making a fibrous loop member according to claim 8 said arcuate portions having an initial height defined as the height of the arcuate portion from the backing during said step of bonding, said roll having a surface, said plate having an inner surface, said surface of said roll and said inner surface of said plate being in facing relation to each other, wherein the distance between the surface of the roll and the inner surface of the plate is at least 10% of the initial height of said arcuate portions.

10. A method for making a fibrous loop member according to claim 8 wherein said plate is curved and concentric with said roll.

11. A fibrous loop member made according to the method of claim 1.

* * * * *

UNITED STATES PATENT AND TRADEMARK OFFICE
CERTIFICATE OF CORRECTION

PATENT NO. : 6,623,587 B1
DATED : September 23, 2003
INVENTOR(S) : Jörg Müller et al.

It is certified that error appears in the above-identified patent and that said Letters Patent is hereby corrected as shown below:

Column 3,
Line 54, delete "Alternatively" and insert therefor -- Alternatively --.

Column 5,
Line 56, delete "Dow Coming" and insert therefor -- Dow Corning --.

Column 7,
Line 56, delete "yams" and insert therefor -- yarns --.

Signed and Sealed this

Twentieth Day of July, 2004

JON W. DUDAS
*Acting Director of the United States Patent and Trademark Office*